United States Patent
Pyle et al.

(10) Patent No.: US 11,931,088 B2
(45) Date of Patent: Mar. 19, 2024

(54) PARALLEL GUIDE FOR MINIMALLY INVASIVE BUNION SURGERY

(71) Applicant: ARTHREX, INC., Naples, FL (US)

(72) Inventors: Casey W. Pyle, Camarillo, CA (US); Thomas G. Harris, La Cañada, CA (US); Alyssa Morgan, Naples, FL (US); Marc Krassler, Gernlinden (DE)

(73) Assignee: Arthrex Inc., Naples, FL (US)

( * ) Notice: Subject to any disclaimer, the term of this patent is extended or adjusted under 35 U.S.C. 154(b) by 289 days.

(21) Appl. No.: 17/397,207

(22) Filed: Aug. 9, 2021

(65) Prior Publication Data

US 2023/0042635 A1 Feb. 9, 2023

(51) Int. Cl.
| | |
|---|---|
| *A61B 17/00* | (2006.01) |
| *A61B 17/17* | (2006.01) |
| *A61B 17/84* | (2006.01) |
| *A61B 17/90* | (2006.01) |

(52) U.S. Cl.
CPC ........ *A61B 17/90* (2021.08); *A61B 17/00234* (2013.01); *A61B 17/1775* (2016.11); *A61B 17/848* (2013.01); *A61B 2017/0092* (2013.01)

(58) Field of Classification Search
CPC ............ A61B 17/1742; A61B 17/1753; A61B 17/1775; A61B 17/1796; A61B 17/90
See application file for complete search history.

(56) References Cited

U.S. PATENT DOCUMENTS

| | | | |
|---|---|---|---|
| 8,821,504 B2* | 9/2014 | Sharkey | A61B 17/8805 606/92 |
| 10,194,926 B2 | 2/2019 | Claes et al. | |
| 10,226,292 B2 | 3/2019 | Lundquist et al. | |
| 10,278,684 B2 | 5/2019 | Knight et al. | |
| 10,603,054 B2 | 3/2020 | Asfora et al. | |
| 10,881,436 B2 | 1/2021 | Muller et al. | |
| 2008/0161820 A1* | 7/2008 | Wack | A61B 17/88 606/96 |
| 2011/0264149 A1 | 10/2011 | Pappalardo et al. | |
| 2017/0196602 A1 | 7/2017 | Lundquist et al. | |
| 2018/0110530 A1* | 4/2018 | Wagner | A61B 17/8061 |

(Continued)

FOREIGN PATENT DOCUMENTS

| | | |
|---|---|---|
| CN | 103622744 | 5/2015 |
| CN | 207356129 | 5/2018 |

OTHER PUBLICATIONS

International Search Report and Written Opinion for International Patent Application No. PCT/US2022/038759 dated Nov. 3, 2022.

*Primary Examiner* — Nicholas W Woodall
(74) *Attorney, Agent, or Firm* — Carlson, Gaskey & Olds, P.C.

(57) ABSTRACT

A surgical guide includes a body including a beveled distal surface configured to being placed against a side of a foot and a proximal surface. The body includes at least one channel that extends between the beveled distal surface and the proximal surface of the body. At least one K-wire is receivable in the at least one channel and is configured to being received in a metatarsal and a capital fragment of the foot. The guide includes a handle, and a preset angle is defined between a longitudinal axis of the body and the beveled distal surface of the body. The preset angle is between approximately 25° and approximately 30°.

9 Claims, 5 Drawing Sheets

(56) References Cited

U.S. PATENT DOCUMENTS

Figure 1:
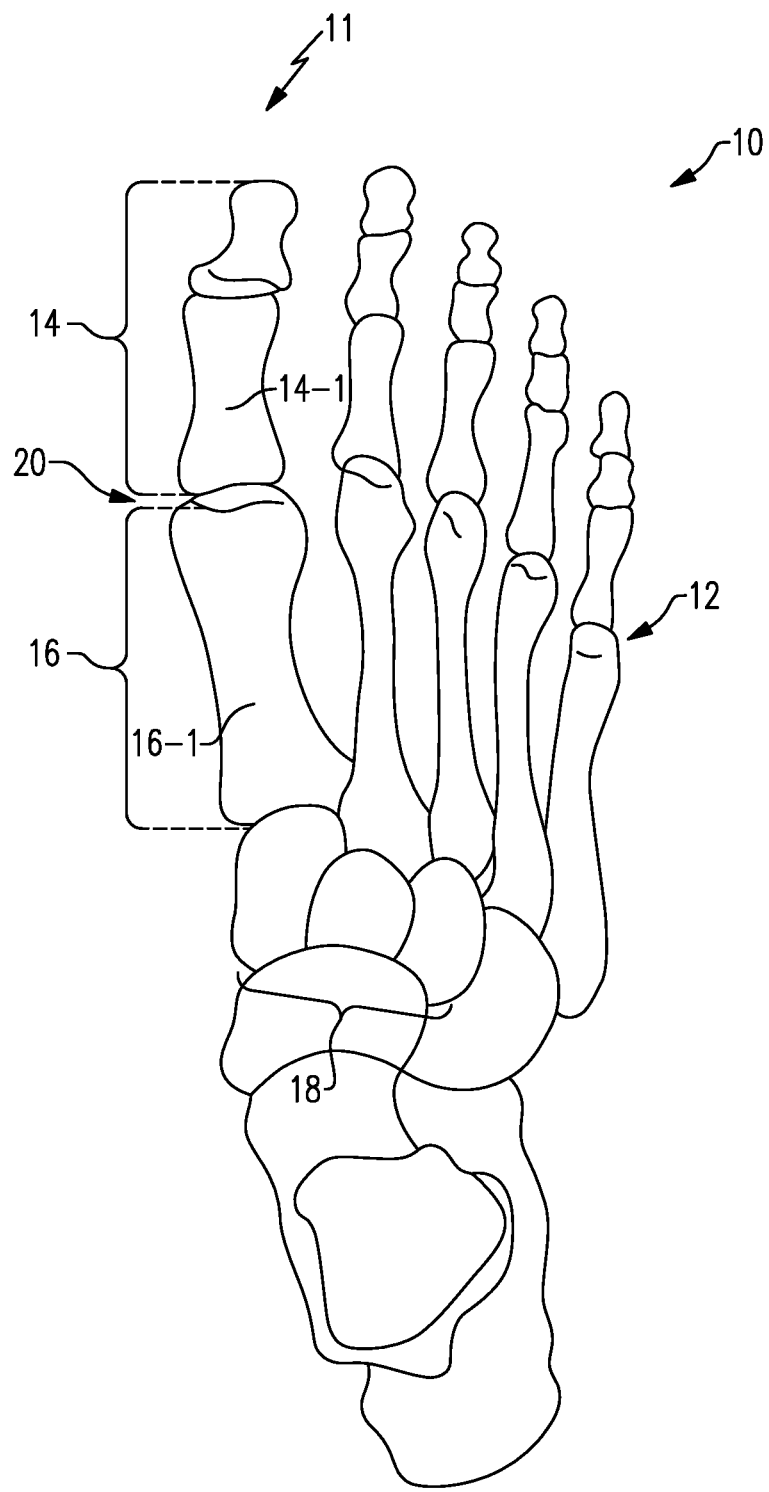

| | | |
|---|---|---|
| 2020/0060698 A1 | 2/2020 | Woodard et al. |
| 2020/0253650 A1 | 8/2020 | Lamm et al. |
| 2021/0022879 A1 | 1/2021 | Hollis et al. |
| 2021/0038260 A1 | 2/2021 | Hollis et al. |

* cited by examiner

PARALLEL GUIDE FOR MINIMALLY INVASIVE BUNION SURGERY

BACKGROUND

This disclosure relates to the field of minimally invasive surgery, and more particularly, to a device and associated instrumentation and surgical methods.

A variety of surgical devices and methods are used to treat bone abnormalities, such as bunions. For example, K-wires are commonly employed during orthopedic surgeries to stabilize and/or align bones or bone fragments to restore functionality to a joint.

SUMMARY

This disclosure is directed to a device and associated instrumentation and surgical methods for performing a minimally invasive surgery.

A surgical guide includes a body having a beveled distal surface configured to being placed against a side of a foot. The body includes a proximal surface and a plurality of aligned channels that extend between the beveled distal surface and the proximal surface of the body. A first K-wire is receivable in one of the plurality of aligned channels, and a second K-wire is receivable in another one of the plurality of aligned channels. A third channel is located between the first channel and the second channel. The guide also includes a handle, and a preset angle is defined between a longitudinal axis of the body and the beveled distal surface of the body. The preset angle is between approximately 25° and approximately 30°, and a pressure is applied with the handle to the surface of the foot that is substantially perpendicular to the surface of the foot. The guide is radiolucent.

A surgical guide includes a body. The body includes a beveled distal surface configured to being placed against a side of a foot and a proximal surface. The body includes at least one channel that extends between the beveled distal surface and the proximal surface of the body. At least one K-wire is receivable in the at least one channel and is configured to being received in a metatarsal and a capital fragment of the foot. The guide includes a handle, and a preset angle is defined between a longitudinal axis of the body and the beveled distal surface of the body.

A method of performing a minimally invasive bunion surgery includes placing a beveled distal surface of a body of a guide on a surface of a foot near a metatarsal. The method further includes inserting a first K-wire through a first channel in the body of the guide that extends from a proximal surface to a beveled distal surface and through the metatarsal and the capital fragment and inserting a second K-wire through a second channel in the body of the guide that extends from the proximal surface to the beveled distal surface and through the metatarsal and the capital fragment. The first channel and the second channel are separated by a third channel.

These and other features of the present disclosure can be best understood from the following specification and drawings, the following of which is a brief description.

DETAILED DESCRIPTION OF THE DRAWINGS

Figure 2:
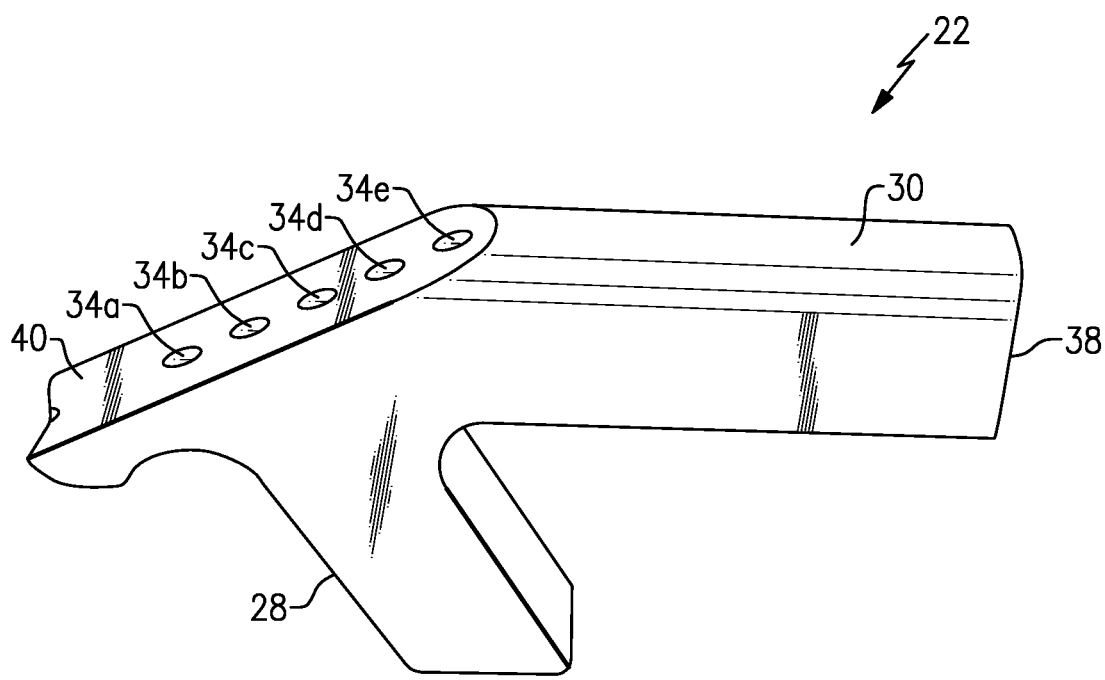
Figure 3:
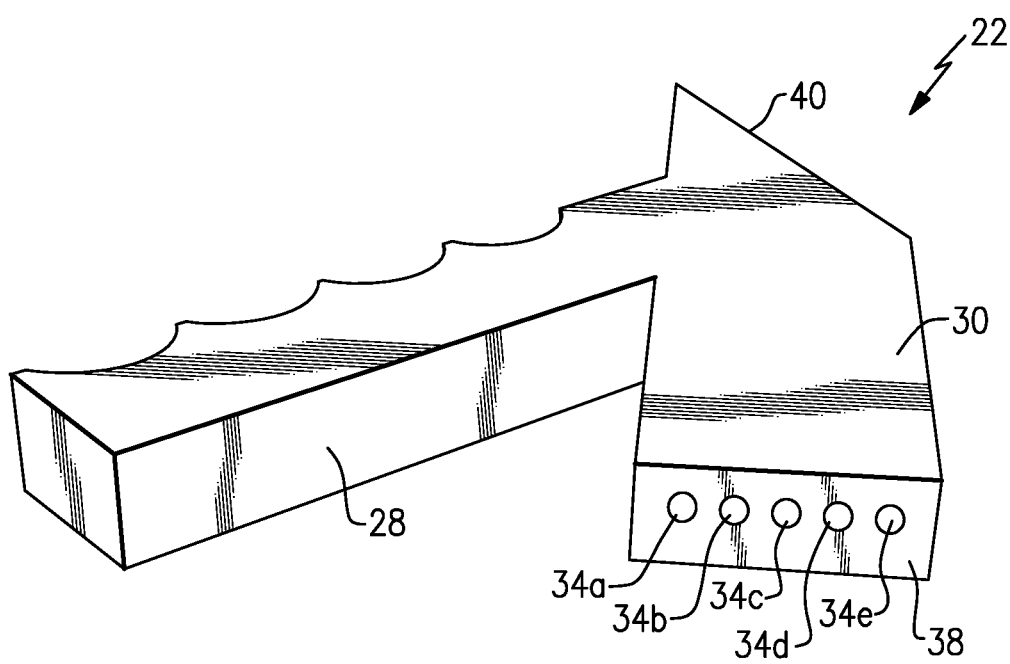
Figure 4:
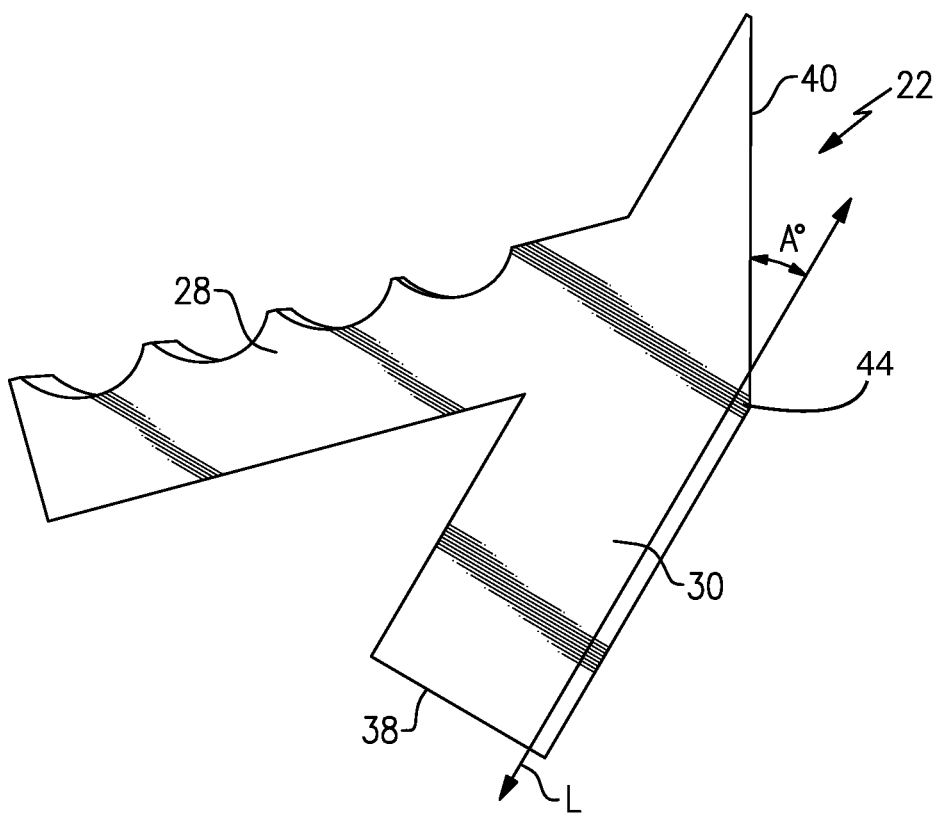
Figure 5:
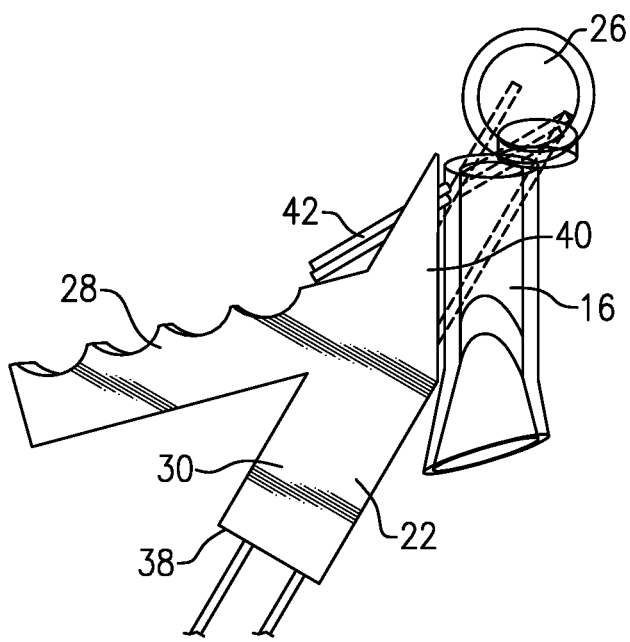
Figure 6:
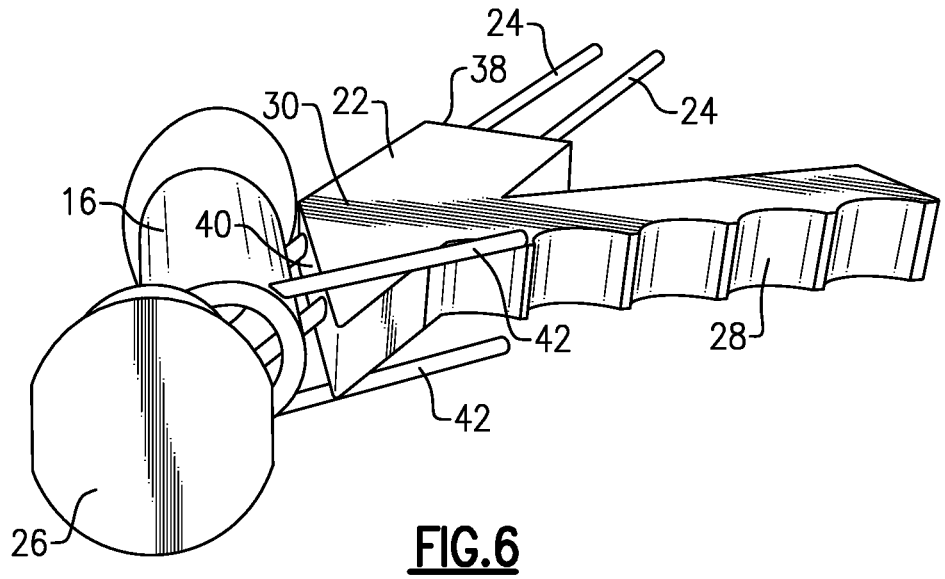
Figure 7:
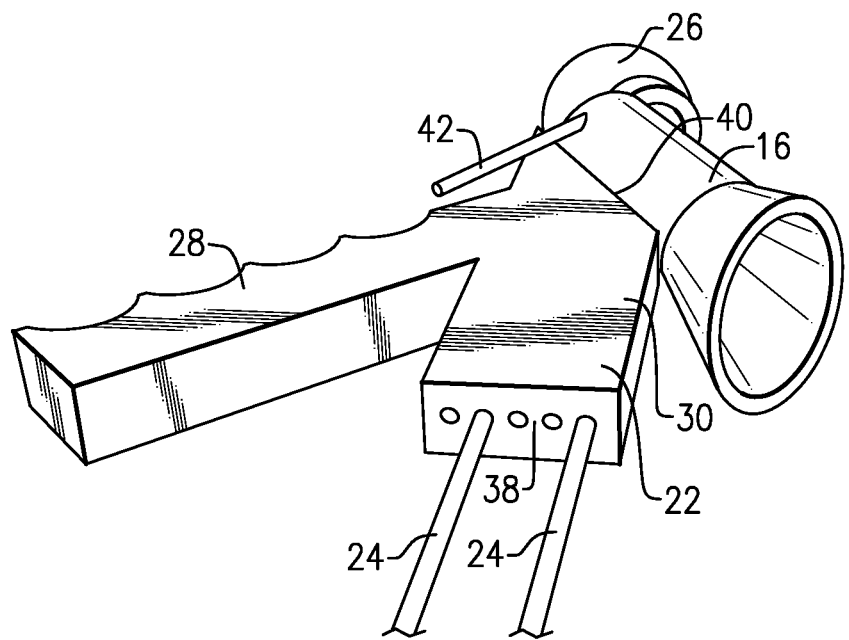
Figure 8:
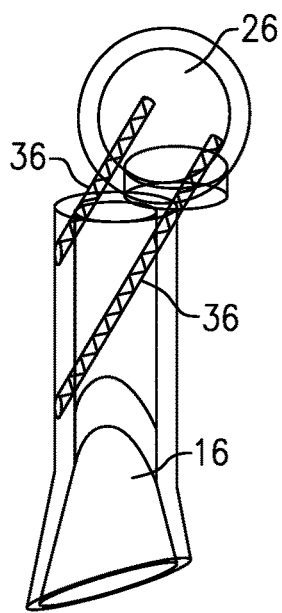
Figure 9:
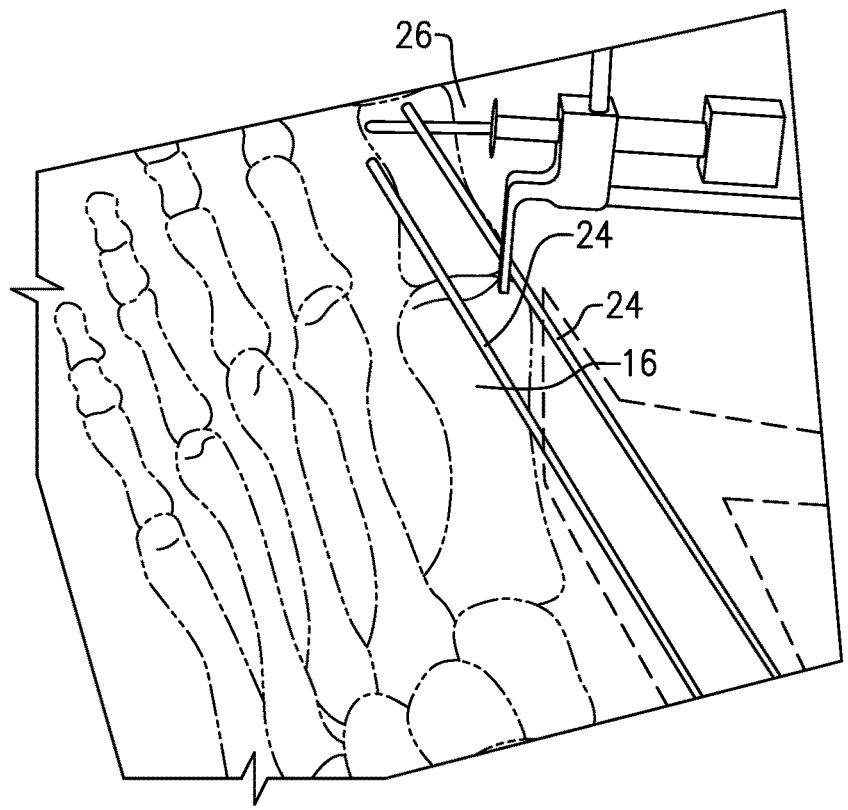

FIG. 1 illustrates a foot of the human musculoskeletal system including a bone abnormality;
FIG. 2 illustrates a top view of a parallel guide used in a minimally invasive surgical bunion procedure;
FIG. 3 illustrates a perspective view of the parallel guide;
FIG. 4 illustrates another top view of the parallel guide;
FIG. 5 illustrates a top view of the parallel guide used to guide two K-wires;
FIG. 6 illustrates a perspective view of the parallel guide used to guide two K-wires;
FIG. 7 illustrates another perspective view of the parallel guide used to guide the two K-wires;
FIG. 8 illustrates a top view the capital fragment secured to the metatarsal with two screws; and
FIG. 9 illustrates an x-ray image of the parallel guide positioned on a surface of the foot.

DETAILED DESCRIPTION

This disclosure is directed to a device and associated instrumentation and surgical methods for performing a minimally invasive surgical procedure. In a specific embodiment, the surgical procedure is to repair a hallux valgus at the metatarsophalangeal (MTP) joint (i.e., bunion).

Exemplary minimally invasive surgical methods may be performed using K-wires to stabilize and/or align bones and/or bone fragments. The exemplary parallel guide is configured to guide K-wires during a bunion surgery. These and other features of this disclosure are described in further detail below.

In one example, a surgical guide includes a body including a beveled distal surface configured to being placed against a side of a foot. The body includes a proximal surface and a plurality of aligned channels that extend between the beveled distal surface and the proximal surface of the body. A first K-wire is receivable in one of the plurality of aligned channels, and a second K-wire is receivable in another one of the plurality of aligned channels. A third channel is located between the first channel and the second channel. The guide also includes a handle, and a preset angle is defined between a longitudinal axis of the body and the beveled distal surface of the body. The preset angle is between approximately 25° and approximately 30°, and a pressure is applied with the handle to the surface of the foot that is substantially perpendicular to the surface of the foot. The guide is radiolucent.

In another embodiment, the preset angle is approximately 25°.

In another embodiment, the preset angle is approximately 30°.

In another embodiment, the preset angle is adjustable. In an embodiment, the preset angle is adjustable from about 25° to about 30°. In an embodiment, the preset angle is adjustable from about 25° to about 35°. In an embodiment, the preset angle is adjustable from about 20° to about 30°. In an embodiment, the preset angle is adjustable from about 24° to about 32°. In an embodiment, the preset angle is adjustable from about 24° to about 31°. In an embodiment, the preset angle is adjustable from about 23° to about 32°. In an embodiment, the preset angle is adjustable from about 23° to about 31°. In an embodiment, the preset angle is adjustable from about 22° to about 32°. In an embodiment, the preset angle is adjustable from about 22° to about 31°.

In another example, a surgical guide includes a body. The body includes a beveled distal surface configured to being placed against a side of a foot and a proximal surface. The body includes at least one channel that extends between the beveled distal surface and the proximal surface of the body. At least one K-wire is receivable in the at least one channel and is configured to being received in a metatarsal and a capital fragment of the foot. The guide includes a handle, and a preset angle is defined between a longitudinal axis of the body and the beveled distal surface of the body. The preset angle is between approximately 25° and approximately 30°.

In another embodiment, the preset angle is approximately 25°.

In another embodiment, the preset angle is approximately 30°.

In another embodiment, the preset angle is adjustable

In another embodiment, the at least one K-wire includes a first K-wire and a second K-wire, and the at least one channel includes a first channel and a second channel. The first K-wire is received in the first channel, the second K-wire is received in the second channel, and a third channel is located between the first channel and the second channel.

In another embodiment, a pressure is applied with the handle of the guide to the surface of the foot that is substantially perpendicular to the surface of the foot.

In another embodiment, the at least one channel includes a plurality of channels.

In another embodiment, the plurality of channels are aligned.

In another embodiment, the guide is radiolucent.

In another example, a method of performing a minimally invasive bunion surgery includes placing a beveled distal surface of a body of a guide on a surface of a foot near a metatarsal. The method includes inserting a first K-wire through a first channel in the body of the guide that extends from a proximal surface to a beveled distal surface and through the metatarsal and the capital fragment and inserting a second K-wire through a second channel in the body of the guide that extends from the proximal surface to the beveled distal surface and through the metatarsal and the capital fragment. The first channel and the second channel are separated by a third channel.

In another embodiment, the method includes performing an osteotomy to shift the capital fragment from the metatarsal.

In another embodiment, the method includes moving at least one guide wire through the metatarsal and the capital fragment in a first direction, laterally translating the capital fragment relative to the metatarsal to a desired position, and moving the at least one guide wire through the metatarsal and the capital fragment in an opposing second direction to prevent lateral and rotational translation of the capital fragment and retain the capital fragment in the desired position.

In another embodiment, the at least one guide wire includes two guide wires, and the method includes placing the beveled distal surface of the body of the guide on the surface of the foot near the metatarsal to locate the guide between the two guide wires.

In another embodiment, the method includes removing the guide from the surface of the foot.

In another embodiment, the method includes advancing a cannulated screw over each of the first K-wire and the second K-wire and removing the first K-wire and the second K-wire from the foot.

In another embodiment, the first channel, the second channel, and the third channel are substantially parallel.

FIG. 1 schematically illustrates a portion of a foot 10 of the human musculoskeletal system. A forefoot 12 of the foot 10 includes multiples phalanges 14 (i.e., toes), multiples metatarsals 16 located proximal to the phalanges 14, and a trio of cuneiforms 18 (i.e., medial, middle, and lateral cuneiforms) located proximal to the metatarsals 16. The foot 10 includes a bone abnormality 20. In one example, the bone abnormality 20 is a hallux valgus abnormality (also referred to as a bunion abnormality) in which there is a medial deviation of a first metatarsal 16-1 and a lateral deviation of a first phalange 14-1 of the hallux 11.

FIGS. 2 to 4 illustrate a parallel guide 22 that guides percutaneous placement of at least two K-wires 24 into a metatarsal 16 and a capital fragment 26 during a minimally invasive surgical bunion procedure for bunion correction. The parallel guide 22 includes a handle 28 and a body 30. The handle 28 of the parallel guide 22 can be held by a surgeon during a minimally invasive surgical bunion procedure to apply pressure with the body 30 against a side of the foot 10. The handle 28 of the parallel guide 22 allows the pressure to be applied substantially perpendicularly to a surface of the foot 10, avoiding slipping of the parallel guide 22 and ensuring proper placement of the parallel guide 22. The parallel guide 22 can be used in a fully percutaneous procedure and is designed to guide K-wires 24 without making incisions for placement of the parallel guide 22 on the foot 10.

A preset angle A° is defined between a longitudinal axis L of the body 30 and a distal surface 40 of the body 30 that is beveled. In one example, the preset angle A° is approximately 25°. In another example, the preset angle A° is approximately 30°. However, the preset angle A° of the parallel guide 22 can be any angle between 25° and 30°. In another example, the preset angle A° of the parallel guide 22 is adjustable using a mechanism 44.

In one example, the preset angle is adjustable from about 25° to about 30°. In an embodiment, the preset angle is adjustable from about 25° to about 35°. In one example, the preset angle is adjustable from about 20° to about 30°. In one example, the preset angle is adjustable from about 24° to about 32°. In one example, the preset angle is adjustable from about 24° to about 31°. In one example, the preset angle is adjustable from about 23° to about 32°. In one example, the preset angle is adjustable from about 23° to about 31°. In one example, the preset angle is adjustable from about 22° to about 32°. In one example, the preset angle is adjustable from about 22° to about 31°.

The preset angle A° of the parallel guide 22 is specifically applicable to a minimally invasive surgical procedure for bunions. When the body 30 of the parallel guide 22 is placed on a surface of the foot 10, a pressure is applied with the handle 28 held by the surgeon that is substantially perpendicular to a surface of the foot 10. The preset angle A° determines an angle of insertion of the K-wires 24 through the body 30 and into the metatarsal 16 and the capital fragment 26.

In one example, the body 30 of the parallel guide 22 includes at least one channel 34 that receives a K-wire 24. In one example, the body 30 of the parallel guide 22 includes a plurality of substantially parallel channels 34 that can each receive a K-wire 24. In one example, the substantially parallel channels 34 are aligned in a straight configuration. In one example, the body 30 includes five parallel channels 34 that pass through a length of the body 30 from a proximal surface 38 of the body 30 to the distal surface 40 of the body 30 that is beveled. The beveled distal surface 40 provides an ideal angle for the trajectory of a K-wire 24.

As the parallel guide 22 includes multiple channels 34, precision and accurate placement of a K-wire 24 in the metatarsal 16 is possible. The channels 34 provide stability to the K-wire 24 along the length of the body 30 to minimize deflection of the K-wire 24.

A desired channel 34a, 34b, 34c, 34d, and 34e of the parallel guide 22 can be selected from the five channels 34 to provide for the ideal placement of the K-wire 24. In one example, two channels 234 are selected. In one example, the channels 34a and 34c can each receive a K-wire 24, leaving the channel 34b empty. In another example, the channels 34c and 34e can each receive a K-wire 24, leaving the channel 34d empty. In another example, the channels 34b and 34d can each receive a K-wire 24, leaving the channel 34c empty.

As shown in FIG. 8, when two K-wires 24 are each positioned in a channel 34 while allowing at least one empty channel 34 between the two K-wires 24 and then drilled into the metatarsal 16, two screws 36 can be located side by side once positioned over the K-wires 24. In one example, each K-wire 24 is a 1.6 mm K-wire 24. In one example, the screws 36 are 4.0 mm beveled fully threaded screws that are used in minimally invasive surgical bunion procedures. The channel 34 spacing between the two K-wires 24 is designed specifically to work with the above-described screws 36.

The channels 34 are distanced and oriented in the body 30 of the parallel guide 22 such that the use of a K-wire 24 in each of two alternating channels 34 allows for two screws 36 to be placed into the capital fragment 26 without the screws 36 intersecting. The body 30 is also slim enough to fit between provisional guide wires 42 (shown in FIGS. 5 to 7 and discussed below) drilled through the metatarsal 16 and the capital fragment 26.

As shown in FIG. 9, the parallel guide 22 is also radiolucent. During a minimally invasive procedure when fluoroscopy is used to determine the placement of the K-wires 24 and the position of the capital fragment 24, the radiolucent parallel guide 22 that receives the K-wires 24 will not affect the visibility of the K-wires 24 in the x-ray images.

An incision can be made at a midline metatarsal 16. An osteotomy can be performed to shift the capital fragment 26 from the metatarsal 16. In an embodiment, at least two guide wires 42 for temporary fixation and that maintain the capital fragment 26 laterally can be advanced by a drill through the metatarsal 16 and the capital fragment 26 in a first direction. Two guide wires 42 can be advanced by the drill until they clear the metatarsal 16 and exit the skin of the hallux 11, allowing the capital fragment 26 to laterally translate relative to the metatarsal 16. An instrument can laterally translate the capital fragment 26 into the desired position. The guide wires 42 can be advanced with the drill in an opposite second direction until the two guide wires 42 abut a proximal aspect of the metatarsal 16 while holding the hallux 11 to prevent lateral and rotational translation of the capital fragment 26 and to maintain the capital fragment 26 in the desired position.

A beveled distal surface 40 of the body 30 of the parallel guide 22 can be placed on the surface of the foot 10 between provisional guide wires 42. Pressure can be applied by the surgeon substantially perpendicular to a surface of the foot 10 through the handle 28 to prevent slipping or ill placement of the parallel guide 22 relative to the side of the foot 10.

While pressure is applied by the parallel guide 22, a K-wire 24 can be inserted into one of the channels 34 and then drilled through the skin and the bone so that the K-wire 24 passes through the metatarsal 16 and the capital fragment 26. While continuing pressure is applied by the parallel guide 22, another K-wire 24 can be inserted into another channel 34 and then drilled through the skin and the bone so that the K-wire 24 passes through the metatarsal 16 and the capital fragment 26. At least one empty channel 34 remains between the two channels 34 that each receive the K-wires 24. Once the K-wires 24 are positioned in the metatarsal 16, fluoroscopy can be employed to determine whether the K-wires 24 are in the proper orientation and/or placement. The parallel guide 22 does not interfere with the images of the K-wires 24 in the x-ray due to its radiolucency.

Once determined that the K-wires 24 are located in the proper position, the parallel guide 22 can be removed from the side of the foot 10. A drill can be used to advance a cannulated screw 36 over each of the K-wires 24 and secure the capital fragment 26 to the metatarsal 16. Once the screws 36 are installed, the K-wires 24 and the guide wires 42 can be removed from the foot 10. Finally, the incision is closed.

The foregoing description is only exemplary of the principles disclosed herein. Many modifications and variations are possible in light of the above teachings.

What is claimed is:

1. A surgical guide comprising:
  a body including a beveled distal surface configured to being placed against a side of a foot, the body including a proximal surface, wherein the body comprises at least one channel that extends between the beveled distal surface and the proximal surface of the body, and at least one K-wire is receivable in the at least one channel and is capable of being received in a metatarsal and a capital fragment of the foot; and
  a handle, wherein a preset angle is defined between a longitudinal axis of the body and the beveled distal surface of the body, and the preset angle is between approximately 25° and approximately 30°, wherein the preset angle is adjustable.

2. The guide as recited in claim 1, wherein the preset angle is approximately 25°.

3. The guide as recited in claim 1, wherein the preset angle is approximately 30°.

4. The guide as recited in claim 1, wherein the at least one K-wire comprises a first K-wire and a second K-wire and the at least one channel comprises a first channel and a second channel, wherein the first K-wire is received in the first channel, the second K-wire is received in the second channel, and a third channel is located between the first channel and the second channel.

5. The guide as recited in claim 1, wherein the handle is configured to receive a pressure that is applied to the surface of the foot that is substantially perpendicular to the surface of the foot.

6. The guide as recited in claim 1, wherein the at least one channel comprises a plurality of channels.

7. The guide as recited in claim 6, wherein the plurality of channels are aligned.

8. The guide according to claim 7, wherein the plurality of aligned channels are substantially parallel.

9. The guide according to claim 1, wherein the guide is radiolucent.

* * * * *